United States Patent [19]

Slater

[11] Patent Number: 4,652,563

[45] Date of Patent: Mar. 24, 1987

[54] VASODILATORS AND β-ADRENOCEPTOR ANTAGONISTS

[75] Inventor: Robert A. Slater, Letchworth, England

[73] Assignee: Smith Kline & French Laboratories Ltd., Welwyn Garden City, England

[21] Appl. No.: 734,520

[22] Filed: May 16, 1985

[30] Foreign Application Priority Data

May 19, 1984 [GB] United Kingdom ................. 8412864

[51] Int. Cl.$^4$ .................... A61K 31/50; C07D 237/04; C07D 205/08; C07D 413/12
[52] U.S. Cl. .................................. 514/247; 540/362; 544/238; 544/239; 548/215; 549/517; 549/560; 560/39; 560/42; 564/425; 564/443; 568/627; 568/648; 568/650; 568/654; 514/913; 514/929
[58] Field of Search ......................... 514/247; 544/239

[56] References Cited

U.S. PATENT DOCUMENTS

| 3,746,712 | 7/1973 | Ross et al. | 544/239 |
| 4,252,984 | 2/1981 | Manoury et al. | 568/27 |
| 4,397,854 | 8/1983 | Sircar | 544/239 |

OTHER PUBLICATIONS

Derwent Abstract 83–785473 (J5 8146–570–A).
Curran et al., *J. Med. Chem.* 17:273–281 (1974).

Primary Examiner—Mark L. Berch
Attorney, Agent, or Firm—Nancy S. Mayer; Stuart R. Suter; Alan D. Lourie

[57] ABSTRACT

This invention relates to dihydropyridazinone compounds having a cyclopropylmethoxyethyl group in the 6-substituent. These compounds are vasodilators and β-adrenoceptor antagonists. A particular compound of the invention is 6-[4-[3-[2-hydroxy-3-[4-(2-(cyclopropylmethoxy)ethyl)phenoxy]propylamino]propionamido]phenyl]-5-methyl-4,5-dihydro-3 (2H)-pyridazinone.

23 Claims, No Drawings

VASODILATORS AND β-ADRENOCEPTOR ANTAGONISTS

This present invention relates to dihydropyridazinones and in particular to such compounds comprising a cyclopropylmethoxyethyl group. This invention further relates to pharmaceutical compositions containing them and to methods of producing vasodilator and β-adrenoceptor antagonist activity. This invention further relates to intermediates useful in the preparation of such compounds. The compounds of this invention are vasodilators and β-adrenoceptor antagonists. In particular it is desirable that they are vasodilators having β-adrenoceptor antagonist activity sufficient to prevent undue tachycardia. Thus they can be used in the treatment of any disease that is conventionally treated with vasodilators, for example, hypertension in particular mild and moderate hypertension. They can also be used in the treatment of any disease that is conventionally treated with β-adrenoceptor antagonists, for example angina, myocardial infarction, arrhythmias, thyrotoxicosis, anxiety, migraine, tremor, glaucoma and congestive heart failure. In addition these compounds have platelet aggregation inhibiting properties and bronchodilating properties. The major utility of the compounds of this invention is in the treatment of hypertension, for such treatment the compounds have a very desirable profile of activity and duration. It is particularly important to have compounds that display at vasodilating doses sufficient β-adrenoceptor activity to prevent undue tachycardia. Likewise it is desirable that at doses effective to cause β-adrenoceptor antagonism sufficient vasodilatation is caused.

Accordingly the present invention provides the compounds of the formula (I):

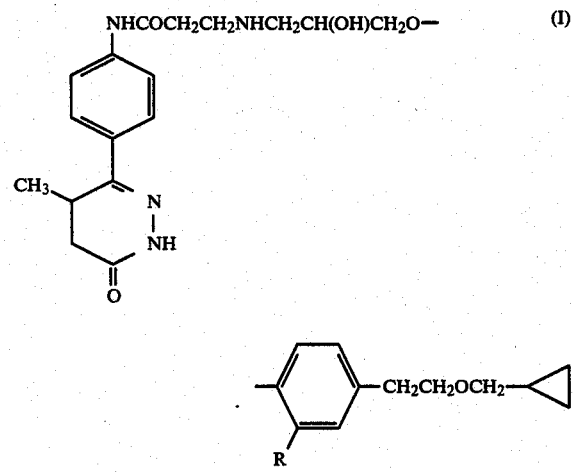

and pharmaceutically acceptable salts thereof, wherein R is hydrogen or $C_{1-4}$alkyl.

Suitably R is $C_{1-4}$alkyl, for example methyl, ethyl, n-propyl or isopropyl.

Preferably R is hydrogen.

Particular compounds of this invention are:
6-[4-[3-[2-hydroxy-3-[4-(2-(cyclopropylmethoxy)ethyl)-phenoxy]propylamino]propionamido]phenyl]-5-methyl-4,5-dihydro-3(2H)-pyridazinone,
6-[4-[3-[2-hydroxy-3-[2-n-propyl-4-(2-(cyclopropylmethoxy)-ethyl)phenoxy]propylamino]propionamido]-phenyl]-5-methyl-4,5-dihydro-3(2H)-pyridazinone, and
6-[4-[3-[2-hydroxy-3-[2-methyl-4-(2-(cyclopropylmethoxy)ethyl)phenoxy]propylamino]propionamido]-phenyl]-5-methyl-4,5-dihydro-3(2H)-pyridazinone.

The compounds of the formula (I) and certain precursors therefor can be obtained in the form of a racemic or diastereoisomeric mixture or as individual isomers (or mixtures thereof). In this specification the first symbol (−) or (+) refers to the sign of rotation of the compound of the formula (VII) used, either directly or indirectly, in the preparation of a compound of the formula (I), and the second symbol (−) or (+) refers to the sign of rotation of the compound of the formula (V) used, either directly or indirectly, in the preparation of a compound of the formula (I). It is believed that these second symbols (−) or (+), relating to the carbon atom bearing the hydroxy group, correspond to the (S) and (R)-configurations respectively.

Suitably the compounds of the formula (I) and their pharmaceutically acceptable salts are provided as a racemic or diastereoisomeric mixture which includes at least one of the (−)(−), (−)(+) and (+)(−) isomers. Preferably the compounds of the formula (I) and their pharmaceutically acceptable salts are provided as a racemic or diastereoisomeric mixture which includes the (−)(−) isomer. In a particular aspect the compounds of the formula (I) and their pharmaceutically acceptable salts are provided enantiomerically enriched in respect of the (−)(−)-isomer. Preferably the (−)(−)-isomer is provided substantially free of the corresponding (−)(+), (+)(−) and (+)(+)-isomers.

The compounds of the formula (I) are depicted as dihydropyridazin-3(2H)-ones, but of course the present invention covers all tautomeric forms thereof, for example the dihydropyridazinol form.

The compounds of the formula (I) can form pharmaceutically acceptable acid addition salts with either organic or inorganic acids, for example those formed with hydrochloric, hydrobromic, hydriodic, methanesulphonic, sulphuric, maleic, fumaric, succinic, acetic, tartaric, citric and lactic acids. Preferred acid addition salts are those formed with hydrochloric or methanesulphonic acid, in particular the mono-methanesulphonate salt.

In order to use a compound of the formula (I) or a pharmaceutically acceptable salt thereof for the therapeutic treatment of humans and animals, in particular in cardiovascular therapy, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt thereof and a pharmaceutically acceptable carrier.

The compounds of the formula (I) and their pharmaceutically acceptable salts may be administered in standard manner for the treatment of the indicated diseases, for example orally, parenterally, rectally, trans-dermally or via trans-mucosal (for example sub-lingual or buccal) administration.

The compounds of the formula (I) and their pharmaceutically acceptable salts which are active when given orally or via sub-lingual or buccal administration can be formulated as syrups, tablets, capsules and lozenges. A syrup formulation will generally consist of a suspension or solution of the compound or salt in a liquid carrier for example, ethanol, glycerine, water, arachis oil or fractionated coconut oil with a flavouring or colouring agent. Where the composition is in the form of a tablet, any pharmaceutical carrier routinely used for preparing solid formulations may be used. Examples of such carriers include various celluloses, magnesium stearate, starch, lactose and sucrose. Where the composition is in the form of a capsule, any routine encapsulation procedure is suitable, for example using the aforementioned carriers in a hard gelatin capsule shell. Where the composition is in the form of a soft gelatin shell capsule any pharmaceutical carrier routinely used for preparing dispersions or suspensions may be utilised, for example aqueous gums, celluloses, silicates or oils and are incorporated in a soft gelatin capsule shell. Tablets and gelatin capsules, both hard and soft shell, may be enteric coated to protect the active ingredient or to control its release. Examples of materials which may be used are shellac, cellulose acetate phthalate, hydroxypropylmethyl cellulose phthalate and polyvinylacetate phthalate.

Typical parenteral compositions consist of a solution or suspension of the compound of the formula (I) or pharmaceutically acceptable salt thereof in a sterile aqueous or non-aqueous carrier optionally containing a parenterally acceptable solvent, which may be an oil, for example polyethylene glycol, polyvinylpyrrolidone, lecithin, arachis oil, or sesame oil.

A typical suppository formulation comprises a compound of the formula (I) or a pharmaceutically acceptable salt thereof which is active when administered in this way, with a binding and/or lubricating agent, for example polymeric glycols, gelatins, cocoa-butter or other low melting vegetable or synthetic waxes or fats.

Typical transdermal formulations comprise a conventional aqueous or non-aqueous vehicle, for example a cream, ointment, lotion or paste or can be in the form of a medicated plaster, patch or membrane.

Typical ophthalmic formulations comprise a compound of the formula (I) or a pharmaceutically acceptable salt thereof, which is active when administered in this way, in the form of an ointment, a solid for example a solid insert suitably having a solid water-soluble polymer as carrier, or a buffered or unbuffered isotonic liquid for example phosphate buffer, isotonic sodium borate, isotonic boric acid or isotonic sodium chloride.

Preferably the composition is in unit dosage form, for example a tablet or capsule.

Each dosage unit for oral administration contains suitably from 0.01 mg/Kg to 40 mg/Kg, and preferably from 0.05 mg/Kg to 5 mg/Kg, and each dosage unit for parenteral administration contains suitably from 0.01 mg/Kg to 10 mg/Kg, of a compound of formula (I) or a pharmaceutically acceptable salt thereof calculated as the free base.

The invention further provides a method of producing vasodilator and $\beta$-adrenoceptor antagonist activity which comprises administering to an animal an effective amount to produce said activity of a compound of the formula (I) or a pharmaceutically acceptable salt thereof.

The daily dosage regimen for oral administration is suitably about 0.01 mg/Kg to 100 mg/Kg, more suitably about 0.1 mg/Kg to 25 mg/Kg of a compound of formula (I) or a pharmaceutically acceptable salt thereof calculated as the free base. The daily dosage regimen for parenteral administration is suitably about 0.01 mg/Kg to 10 mg/Kg, more suitably about 0.01 mg/Kg to 2.5 mg/Kg, of a compound of the formula (I) or a pharmaceutically acceptable salt thereof calculated as the free base. The active ingredient may be administered from 1 to 4 times a day, sufficient to effect vasodilatation and/or $\beta$-adrenoceptor antagonism. For ocular administration suitably 0.01 to 30 mg of the compound of the formula (I) or pharmaceutically acceptable salt thereof (calculated as the free base) is administered daily, in 1 to 6 doses. Suitable concentrations for the active compound in the carrier are 0.01 to 25% dependent on the nature of the carrier; typical concentrations for eye drop solutions are 0.25–0.5% suitably containing 1–5 mg of active compound.

The compounds of this invention may be co-administered with other pharmaceutically active compounds, for example in combination, concurrently or sequentially. Conveniently the compounds of this invention and the other active compound or compounds are formulated in a pharmaceutical composition. Examples of compounds which may be included in pharmaceutical compositions with the compounds of the formula (I) are vasodilators for example hydralazine, angiotensin converting enzyme inhibitors for example captopril, antianginal agents for example isosorbide nitrate, glyceryl trinitrate and pentaerythritol tetranitrate, anti-arrhythmic agents for example quinidine, procainamide and lidocaine, cardioglycosides for example digoxin and digitoxin, calcium antagonists for example verapamil and nifedipine, diuretics such as thiazides and related compounds for example bendrofluazide, chlorothiazide, chlorothalidone, hydrochlorothiazide, and other diuretics for example frusemide and triamterene, and sedatives for example nitrazepam, flurazepam and diazepam.

The compound of the formula (I) and pharmaceutically acceptable salts thereof can be prepared by a process which comprises:

(a) reacting a compound of the formula (II) with a compound of the formula (III):

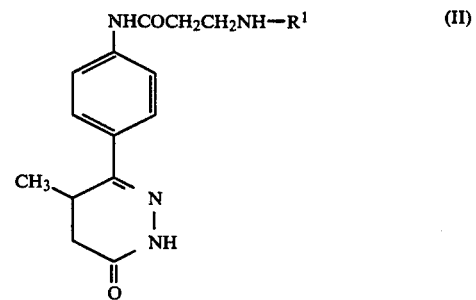

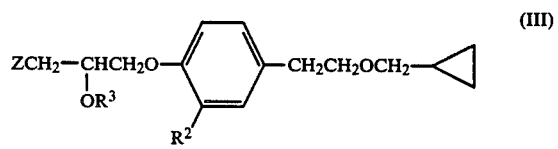

wherein $R^1$ is hydrogen or a protecting group and $R^2$ is a group R is defined in relation to formula (I) or is an alkylene precursor therefor, Z is a leaving group and $R^3$ is hydrogen or a protecting group or Z and $R^3$ together form a bond so as to form an epoxide: or (b) reacting a compound of the formula (IV) with a compound of the formula (V):

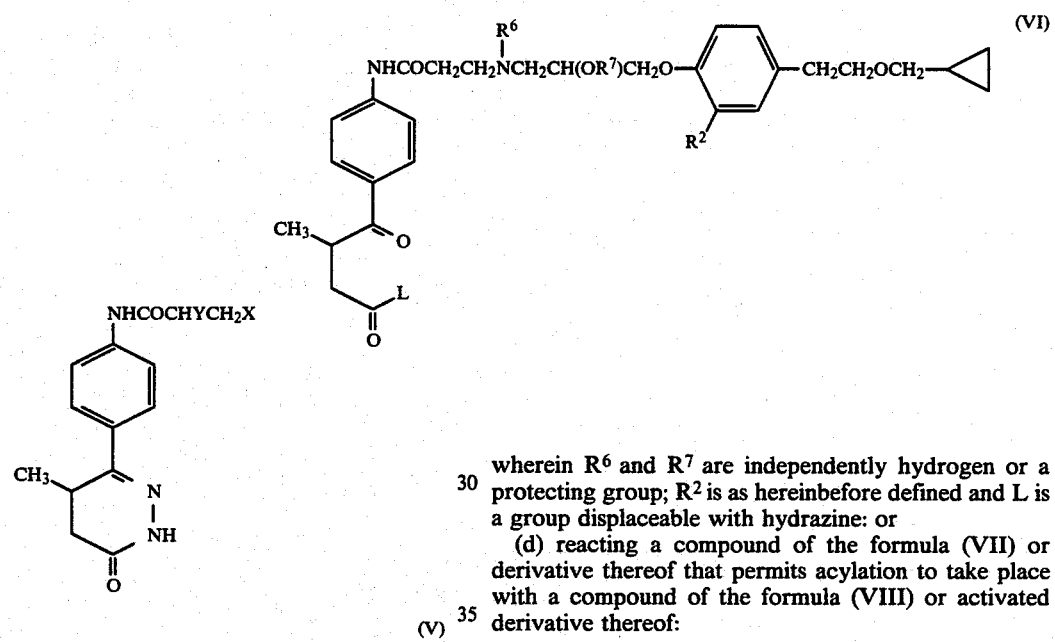

(IV)

(V)

wherein X is a moiety displaceable by amine and Y is hydrogen or X and Y together represent a bond (so as to form a double bond), $R^2$ is as hereinbefore defined, and $R^4$ and $R^5$ are independently hydrogen or a protecting group: or (c) reacting a compound of the formula (VI) with hydrazine or the chemical equivalent thereof:

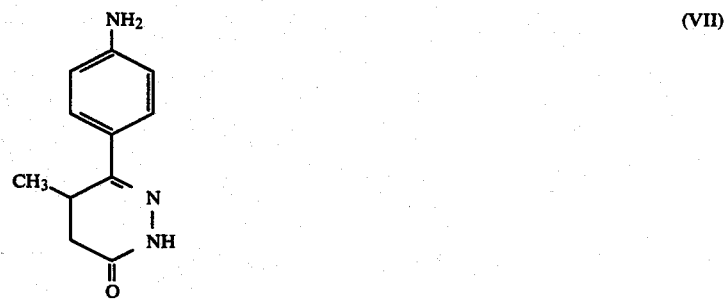

(VI)

wherein $R^6$ and $R^7$ are independently hydrogen or a protecting group; $R^2$ is as hereinbefore defined and L is a group displaceable with hydrazine: or (d) reacting a compound of the formula (VII) or derivative thereof that permits acylation to take place with a compound of the formula (VIII) or activated derivative thereof:

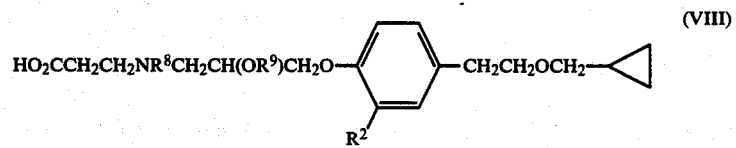

(VII)

(VIII)

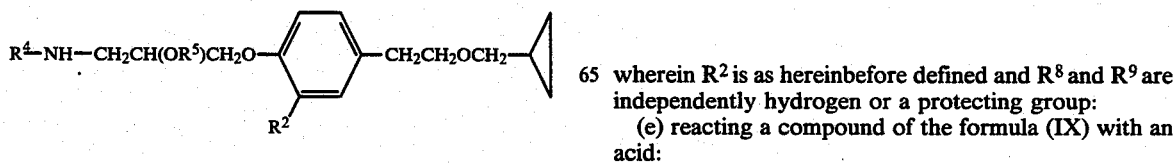

wherein $R^2$ is as hereinbefore defined and $R^8$ and $R^9$ are independently hydrogen or a protecting group:

(e) reacting a compound of the formula (IX) with an acid:

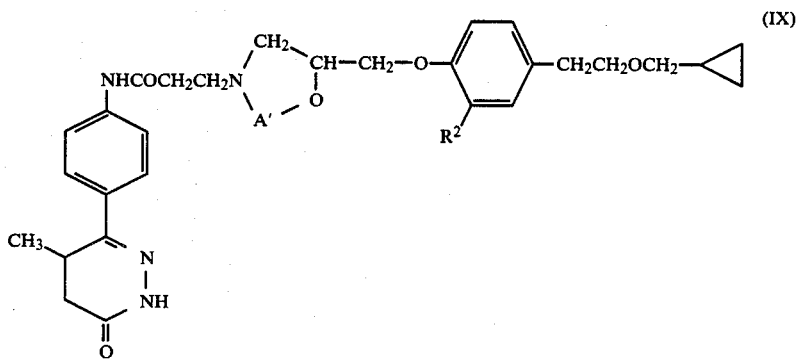

wherein $R^2$ is as hereinbefore defined, and $A'$ is an acid-cleavable optionally substituted methylene protecting group for the N— and O— atoms: or (f) reacting a compound of the formula (X) with an anion of the formula (XI):

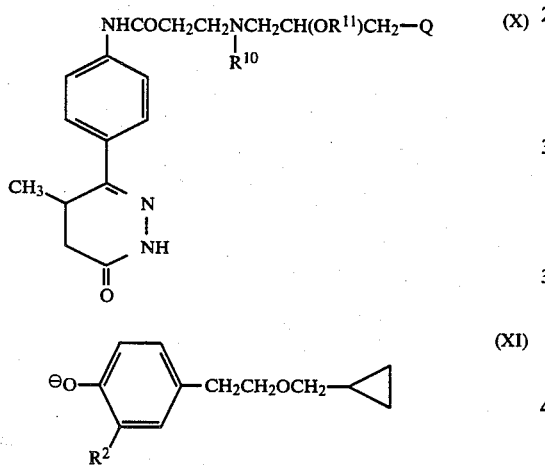

wherein $R^2$ is as hereinbefore defined, $R^{10}$ and $R^{11}$ are independently hydrogen or protecting groups, and Q is a displaceable group, or $R^{11}$ and Q together form a bond so as to form an epoxide: and thereafter, if necessary:

(i) removing any protecting group;
(ii) converting a group $R^2$ wherein $R^2$ is an alkylene precursor to a group R;
(iii) forming a pharmaceutically acceptable salt.

In the compounds of the formulae (III), (V), (VI), (VIII), (IX) and (XI) suitably $R^2$ is a group R, that is hydrogen or $C_{1-4}$alkyl. In an alternative suitable aspect $R^2$ is an alkylene precursor, that is $C_{2-4}$alkylene for example allyl which may be converted to n-propyl for example by hydrogenation.

Suitable N-protecting groups $R^1$, $R^4$, $R^6$ and $R^8$ and $R^{10}$ are those conventional in the art, for example see "Protective Groups in Organic Synthesis", T. W. Greene 1981 (Wiley). Suitably N-protecting groups are those cleavable by hydrogenation or hydrolysis, using conditions that do not substantially affect the remainder of the molecule. For example N-protecting groups include optionally substituted benzyl for example benzyl and nitrobenzyl, benzhydryl, trityl, trifluoroacetyl, $C_{1-10}$alkanoyl for example acetyl, $(C_2H_5O)_2P(=O)$—, and optionally substituted alkoxymethyl. Favourably in the reaction sequences described herein, any N-protecting group is benzyl.

Suitable O-protecting groups, $R^3$, $R^5$, $R^7$, $R^9$ and $R^{11}$ are those conventional in the β-adrenoceptor art and those appropriate groups known in standard textbooks, for example "Protective Groups in Organic Synthesis", T. W. Greene 1981 (Wiley). Suitably O-protecting groups are those cleavable by hydrogenation or hydrolysis, using conditions that do not substantially affect the remainder of the molecule. For example O-protecting groups include ether forming moieties such as optionally substituted benzyl for example benzyl and nitrobenzyl, benzhydryl, trityl, optionally substituted benzyloxymethyl, $C_{1-6}$alkoxymethyl, for example methoxymethyl, silyl for example trimethylsilyl and tetrahydropyranyl. In addition examples of O-protecting groups include acyl groups such as optionally substituted benzyloxycarbonyl, $C_{1-10}$alkanoyl for example acetyl, trifluoroacetyl, $C_{1-10}$alkoxycarbonyl for example t-butoxycarbonyl or optionally substituted benzoyl. Favourably in the reaction sequences described herein the groups $R^3$, $R^5$, $R^7$, $R^9$ and $R^{11}$ are hydrogen.

Suitably hydrogenation is performed in conventional manner under catalytic conditions using for example conventional transition metal catalysts such as palladium on a suitable carrier with hydrogen gas or under conditions of catalytic transfer hydrogenation. For example palladium on carbon and palladium hydroxide on carbon may be used. The hydrogenation with hydrogen gas may be performed at non-extreme pressure, for example at atmospheric pressure or at pressures of up to 10 atmospheres ($10.13 \times 10^5$ Pa), preferably at about 3 to 4 atmospheres (3 to $4 \times 10^5$ Pa). Suitably hydrogenation is performed in a $C_{1-4}$alkanol for example ethanol. Catalytic transfer hydrogenation can be effected for example using hydrazine or formic acid.

Suitably hydrolysis is performed under conventional conditions, appropriate to the protecting group, for example basic hydrolysis with dilute hydroxide or acidic hydrolysis with mineral acid.

It should be realised, of course, that suitable N- and/or O-protecting groups should be selected so as not to cause substantial degradation of the remainder of the molecule under the conditions of deprotection.

Therefore in another aspect the present invention provides a process for preparing a compound of the formula (I) or a pharmaceutically acceptable salt thereof which comprises deprotecting or converting a compound of the formula (IA):

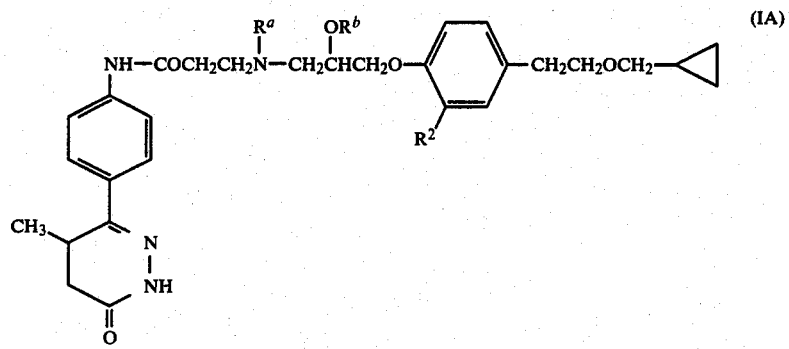

wherein R² is as hereinbefore defined and Rᵃ and Rᵇ are independently hydrogen or protecting groups, with the proviso that when R² is a group R (as hereinbefore defined) Rᵃ and Rᵇ are not both hydrogen, and thereafter if desired forming a pharmaceutically acceptable salt. Suitable groups Rᵃ are those as defined hereinbefore with respect to groups R¹, R⁴, R⁶, R⁸ and R¹⁰. Suitable groups Rᵇ are those as defined hereinbefore with respect to groups R³, R⁵, R⁷, R⁹ and R¹¹.

The compounds of the formula (I) can be conveniently prepared in racemic form, in the form of a mixture of diastereoisomers, in the form of enantiomerically enriched material or in the form of one isomer substantially free of other isomers. The processes of this invention may be adapted accordingly, selecting appropriate chiral starting-materials and intermediates as necessary, and/or resolving certain intermediates in conventional manner. In general the processes of this invention are applicable to the preparation of any desired form, but care should be taken that neither chiral centre racemises during the processes, for example the 5-methyl substitutent of the dihydropyridazinone ring may racemise under strong acid conditions.

Pharmaceutically acceptable salts of the compounds of the formula (I) may be prepared in conventional manner, for example acid addition salts may be prepared by treating the compounds of the formula (I) with the appropriate acid in a $C_{1-4}$alkanol, or they may be prepared by the use of an ion-exchange resin to form the free base or via a different acid addition salt.

In the reaction between a compound of the formula (II) and a compound of the formula (III) Z is suitably a sulphonate such as a $C_{1-6}$alkanesulphonate for example methanesulphonate or an arylsulphonate for example benzenesulphonate or p-toluenesulphonate, or Z is halo for example bromo or chloro. Preferably Z and R³ together form a bond so as to form an epoxide. This reaction, wherein Z is a leaving group or wherein Z and R³ together form a bond, is suitably carried out in a substantially inert organic solvent such as dichloromethane, chloroform, toluene, xylene, or a $C_{1-4}$alkanol, in particular methanol, ethanol or n-propanol. The reaction is suitably conducted at an elevated temperature such as 50°-150° C., conveniently the reflux temperature of the solvent. Suitably in the reaction between the compounds of the formulae (II) and (III) R¹ is hydrogen, preferably R¹ is a protecting group, in particular benzyl.

The compounds of the formula (II) can be prepared by reacting a compound of the formula (IV) as hereinbefore defined with a compound of the formula NH₂R¹ or with a compound capable of introducing a group —NHR¹ wherein R¹ is as hereinbefore defined, optionally in the presence of a base. For example for introducing a primary amino group (—NH₂), reagents such as hexamethylenetetramine may be used in conventional manner. Suitably R¹ is hydrogen. Preferably R¹ is a protecting group such as benzyl. Suitably X is a sulphonate for example toluene-p-sulphonate, benzenesulphonate or an $C_{1-6}$alkanesulphonate for example methanesulphonate, a carboxylate, hydroxy or alkoxy. Preferably X is a halo moiety for example chloro or bromo. This reaction is suitably performed in a substantially inert organic solvent such as dioxan, tetrahydrofuran, dimethylformamide, acetonitrile, dichloromethane, chloroform, toluene, xylene, or an $C_{1-4}$alkanol; in particular acetonitrile, methanol, ethanol or n-propanol. The reaction is suitably conducted at an elevated temperature such as 50°-150° C., conveniently the reflux temperature of the solvent. Suitably the base is an organic amine such as a tri-n-alkylamine for example triethylamine or tri-n-propylamine.

In an alternative the compounds of the formula (II) can be prepared by methods known in the art, see for example No. EP-A-117403. For example by reacting a compound of the formula (VII) or derivative thereof that permits acylation to occur with an activated derivative of a compound of the formula (XII):

HOOCCH₂CH₂NHR¹            (XII)

wherein R¹ is as hereinbefore defined. Suitably the activated derivative takes the form of an acid halide for example an acid chloride, and the reaction is performed in conventional manner for example at an elevated temperature in a substantially inert solvent.

The compounds of the formula (III) wherein Z and R³ form a bond so as to form an epoxide can be prepared by the methods of U.S. Pat. No. 4,252,984. The compounds of the formula (III) wherein Z is a leaving group can be prepared in conventional manner, for example reacting an appropriately substituted phenol with a glycerol derivative: HOCH₂CH(OH)CH₂Q wherein Q is as hereinbefore defined, both hydroxy groups being protected, subsequently deprotecting and converting the primary hydroxy group to a group Z.

The compounds of the formula (IV) can be prepared by known methods, for example by reacting a compound of the formula (VII) or derivative thereof that permits acylation to occur as hereinbefore defined with an activated derivative of a compound of the formula (XIII):

HO₂CCHYCH₂X            (XIII)

wherein X and Y are as hereinbefore defined. Suitably Y is hydrogen, X is a displaceable group and the activated derivative takes the form of an acid halide for example an acid chloride. Suitably the reaction is performed at an non-extreme temperature in a substantially inert solvent, for example in toluene under reflux or in a chlorinated hydrocarbon for example dichloromethane at ambient temperature. The compound of the formula (IV) wherein X and Y represent a bond is disclosed as Example 1 in No. DE-A-3209158. The compounds of the formula (IV) wherein Y is hydrogen and X is halo are disclosed in U.S. Pat. No. 4,376,771.

The compound of the formula (VII) is known from Curran et al., J. Medicinal Chemistry, 17, p273 (1974).

The reaction between a compound of the formula (IV) and a compound of the formula (V) occurs under similar conditions as described above for the reaction of compounds of the formulae (IV) and $NH_2R^1$. That is the reaction is performed optionally in the presence of a base. Suitably $R^4$ is hydrogen. Preferably $R^4$ is a protecting group such as benzyl. Suitably X is a sulphonate for example toluene-p-sulphonate, benzenesulphonate or an $C_{1-6}$alkane sulphonate for example methanesulphonate, a carboxylate, hydroxy or alkoxy. Preferably X is a halo moiety for example chloro or bromo. This reaction is suitably performed in a substantially inert organic solvent such as dioxan, tetrahydrofuran, dimethylformamide, acetonitrile, dichloromethane, chloroform, toluene, xylene, or an $C_{1-4}$alkanol; in particular acetonitrile, methanol, ethanol or n-propanol. The reaction is suitably conducted at an elevated temperature such as 50°–150° C., conveniently the reflux temperature of the solvent. Suitably the base is an organic amine such as a tri-n-alkylamine for example triethylamine or tri-n-propylamine.

The compounds of the formula (V) can be prepared by reacting a compound of the formula (III) as hereinbefore defined, preferably wherein Z and $R^3$ form a bond, with a compound of the formula $NH_2R^4$ wherein $R^4$ is as hereinbefore defined or with a compound capable of introducing a group —$NHR^4$, for example for introducing a primary amino group (—$NH_2$), reagents such as hexamethylenetetramine may be used in conventional manner. This reaction takes place under similar conditions as described above for the reaction of compounds of the formulae (II) and (III).

In another aspect the compounds of the formula (V) wherein $R^4$ is a protecting group and $R^5$ is hydrogen can be prepared by reacting a compound of the formula (XIV) with acid:

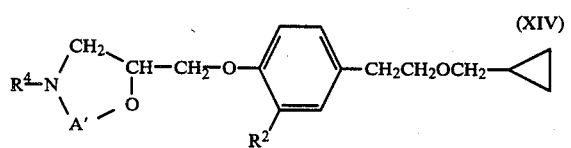

(XIV)

wherein $R^2$ and A' are as hereinbefore defined. Suitably A' is —$C(R^{12})(R^{13})$— wherein $R^{12}$ and $R^{13}$ are independently $C_{1-6}$alkyl, for example they are both methyl. Suitably also A' is optionally substituted —CH(Ph)—, preferably A' is —CH(Ph)—. Suitably such a reaction is performed in an aqueous or mixed aqueous solvent system. Conveniently concentrated hydrochloric acid is used.

The compounds of the formula (XIV) are conveniently prepared from a compound of the formula (XV):

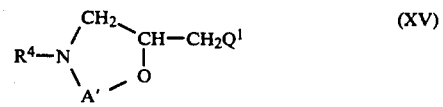

(XV)

wherein A' and $R^4$ are as hereinbefore defined and $Q^1$ is a displaceable group and an anion of the formula (XI) as hereinbefore defined.

In the compounds of the formula (XV) suitably $Q^1$ is a sulphonate such as a $C_{1-6}$alkanesulphonate for example methanesulphonate or an arylsulphonate for example benzenesulphonate or toluene-p-sulphonate, or $Q^1$ is halo for example bromo or chloro. The anion of the formula (XI) is conveniently formed in situ from the corresponding phenol. The anion of the formula (XI) is conveniently generated by the action of base, for example an alkali metal hydroxide or alkaline earth metal hydroxide, for example sodium hydroxide, or for example an organic base such as triethylamine. In a suitable alternative the anion of the formula (XI) is introduced into the reaction as the alkali metal salt of the phenolate, for example the sodium or potassium salt. The reaction between the compound of the formula (XV) and an anion of the formula (XI) is conveniently performed in a solvent such as a $C_{1-4}$alkanol for example methanol or ethanol.

The compound of the formula (XV) can be prepared by reacting a compound of the formula (XVI) with a compound capable of introducing the group $Q^1$:

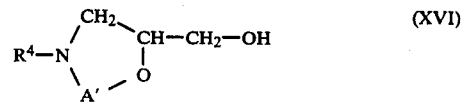

(XVI)

wherein $R^4$ and A' are as hereinbefore defined.

Suitable reagents for introducing the group $Q^1$ are sulphonylating agents for example methanesulphonyl chloride, benzenesulphonyl chloride and toluene-p-sulphonyl chloride; and halogenating agents for example thionyl chloride or thionyl bromide, used in conventional manner.

The compounds of the formula (XVI) can be prepared in conventional manner by reacting an appropriate precursor, for example a ketone or optionally substituted benzaldehyde, with a compound of the formula: $R^4NHCH_2CH(OH)CH_2OH$.

The compounds of the formula: $R^4NHCH_2CH(OH)CH_2OH$ can be prepared by reacting a compound of the formula: $R^4NH_2$ with a compound of the formula: $CHOCH(OH)CH_2OH$ in the presence of a reducing agent, for example hydrogen and a transition metal catalyst.

Preferably in the compound of the formula: $R^4NHCH_2CH(OH)CH_2OH$ and in the sequence of reactions using compounds of the formulae (XVI), (XV) and (XIII), $R^4$ is benzyl.

The reaction between a compound of the formula (VI) and hydrazine or chemical equivalent thereof is suitably performed at ambient or elevated temperature, for example 15°–120° C., preferably about 30°–80° C. or at reflux temperature of a suitable solvent. The reaction is conveniently performed in a solvent such as methanol, ethanol, propanol, aqueous or glacial acetic acid.

Suitably in the compound of the formula (VI) L is hydroxy, $C_{1-6}$alkoxy, amino or $C_{1-6}$alkylamino.

The compounds of the formula (VI) can be prepared from a compound of the formula (XVII) and a compound of the formula (III) in a process analogous to that described for the compounds of the formulae (II) and (III):

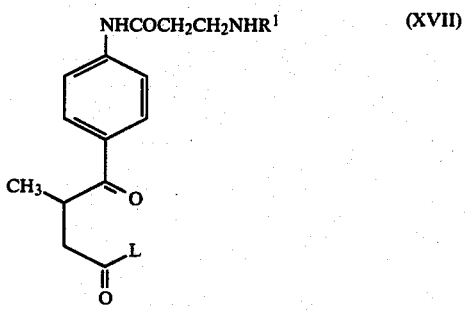
(XVII)

wherein L and $R^1$ are as hereinbefore defined.

The compounds of the formula (XVII) can be prepared from compounds of the formula (XVIII):

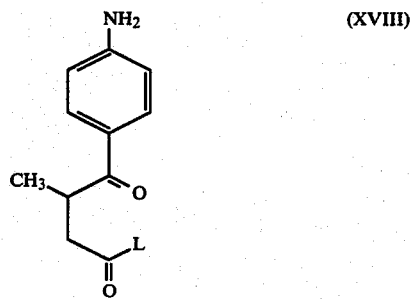
(XVIII)

wherein L is as hereinbefore defined, by methods analogous to those described hereinabove for dihydropyridazinones. The compounds of the formula (XVIII) may be prepared by the methods of McEvoy et al., J. Medicinal Chemistry, 17 p281 (1974).

The reaction between a compound of the formula (VII) and a compound of the formula (VIII) or activated derivative thereof can be performed in conventional manner. Conventional forms of activation, as known in the art, are suitable; and include azetidinones formed by internal cyclization:

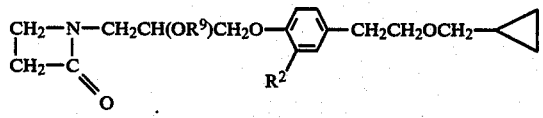

Suitably the activated derivative takes the form of an acid halide for example an acid chloride. Suitably the reaction is performed at an elevated temperature in a substantially inert solvent, for example in toluene under reflux.

The compounds of the formula (VIII) can be prepared from compounds of the formula (III) in conventional manner, for example reaction with a protected 3-aminopropionic acid.

The reaction of a compound of the formula (IX) with acid is suitably performed in an aqueous or mixed aqueous solvent system. Conveniently concentrated hydrochloric acid is used. In the compounds of the formula (IX) suitably A' is $-C(R^{12})(R^{13})-$ wherein $R^{12}$ and $R^{13}$ are independently $C_{1-6}$alkyl, for example they are both methyl. Suitably also A' is optionally substituted $-CH(Ph)-$, preferably A' is $-CH(Ph)-$.

The compounds of the formula (IX) are conveniently prepared from a compound of the formula (XIX):

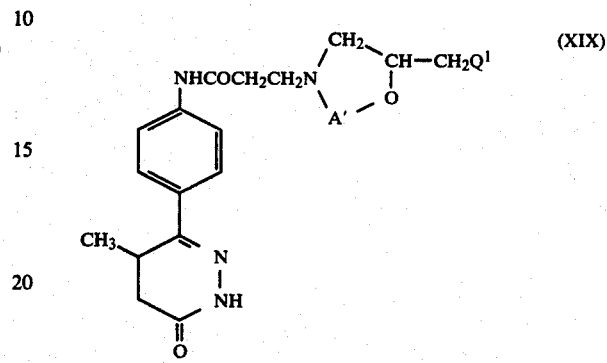
(XIX)

wherein A' and $Q^1$ are as hereinbefore defined and an anion of the formula (XI) as hereinbefore defined.

In the compounds of the formula (XIX) suitably $Q^1$ is a sulphonate such as a $C_{1-6}$alkanesulphonate for example methanesulphonate or an arylsulphonate for example benzenesulphonate or toluene-p-sulphonate, or $Q^1$ is halo for example bromo or chloro. The anion of the formula (XI) is conveniently formed in situ from the corresponding phenol. The anion of the formula (XI) is conveniently generated by the action of base, for example an alkali metal hydroxide or alkaline earth metal hydroxide, for example sodium hydroxide, or for example an organic base such as triethylamine. In a suitable alternative the anion of the formula (XI) is introduced into the reaction as the alkali metal salt of the phenolate, for example the sodium or potassium salt. The reaction between the compound of the formula (XIX) and an anion of the formula (XI) is conveniently performed in a solvent such as a $C_{1-4}$alkanol for example methanol or ethanol.

The compound of the formula (XIX) can be prepared by reacting a compound of the formula (XX) with a compound capable of introducing the group $Q^1$:

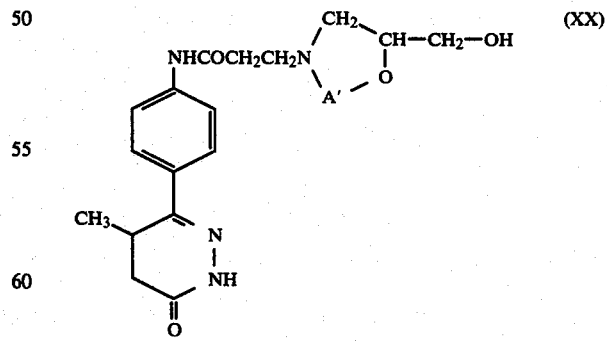
(XX)

wherein A' is as hereinbefore defined.

Suitable reagents for introducing the group $Q^1$ are sulphonylating agents for example methanesulphonyl chloride, benzenesulphonyl chloride and toluene-p-sulphonyl chloride; and halogenating agents for example thionyl chloride or thionyl bromide, used in conventional manner.

The compounds of the formula (XX) can be prepared in conventional manner by reacting an appropriate precursor, for example a ketone or optionally substituted benzaldehyde, with a compound of the formula (XXI):

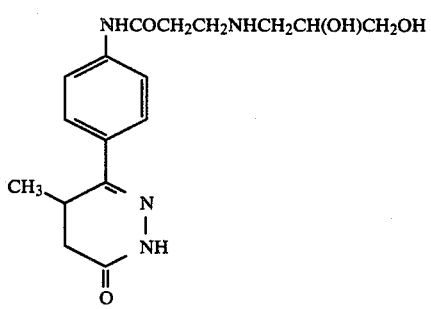

NHCOCH₂CH₂NHCH₂CH(OH)CH₂OH   (XXI)

The compound of the formula (XXI) can be formed by reacting a compound of the formula (II) wherein $R^1$ is hydrogen with a compound of the formula (XXII);

(XXII)

wherein $CR_2$ is a protecting group, for example R is hydrogen or methyl, in the presence of a reducing agent, for example hydrogen and a transition metal catalyst, and subsequently deprotecting to form the diol, for example deprotecting by acid hydrolysis.

In the compounds of the formula (X) suitably Q is a sulphonate such as a $C_{1-6}$alkanesulphonate for example methanesulphonate or an arylsulphonate for example benzenesulphonate or toluene-p-sulphonate, or Q is halo for example bromo or chloro. The anion of the formula (XI) is conveniently formed in situ from the corresponding phenol. The anion of the formula (XI) is conveniently generated by the action of base, for example an alkali metal hydroxide or alkaline earth metal hydroxide, for example sodium hydroxide, or for example an organic base such as triethylamine. In a suitable alternative the anion of the formula (XI) is introduced into the reaction as the alkali metal salt of the phenolate, for example the sodium or potassium salt. The reaction between the compound of the formula (X) and an anion of the formula (XI) is conveniently performed in a solvent such as a $C_{1-4}$alkanol for example methanol or ethanol.

The compound of the formula (X) wherein Q is a displaceable group can be prepared by reacting a compound of the formula (XXIII) with a compound capable of introducing the group Q:

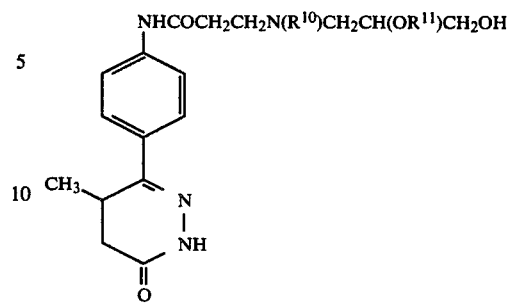

NHCOCH₂CH₂N(R¹⁰)CH₂CH(OR¹¹)CH₂OH   (XXIII)

wherein $R^{10}$ and $R^{11}$ are as hereinbefore defined. Suitable reagents for introducing the group $Q^1$ are sulphonylating agents for example methanesulphonyl chloride, benzenesulphonyl chloride and toluene-p-sulphonyl chloride; and halogenating agents for example thionyl chloride or thionyl bromide, used in conventional manner.

The compound of the formula (XXIII) can be prepared by deprotecting for example by acid hydrolysis, a compound of the formula (XXIV):

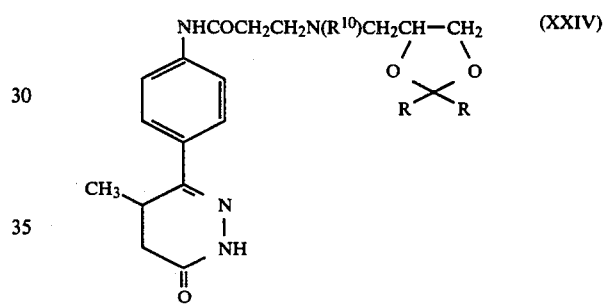

NHCOCH₂CH₂N(R¹⁰)CH₂CH—CH₂   (XXIV)

wherein $R^{10}$ is as hereinbefore defined and $R_2C$ is a protecting group, for example R is hydrogen or $C_{1-6}$alkyl such as methyl. The compounds of the formula (XXIV) can be prepared by reacting a compound of the formula (II) wherein $R^1$ is hydrogen with a compound of the formula (XXII) as hereinbefore defined, in the presence of a reducing agent, for example hydrogen and a transition metal catalyst, and subsequently protecting the amino function.

The compounds of the formula (X) wherein $R^{11}$ and Q together form a bond so as to form an epoxide can be prepared in conventional manner, such as base treatment of an acetoxy bromide (partial structure: —N(R¹⁰)CH₂CH(OCOCH₃)CH₂Br) which can be prepared from a compound of the formula (XXIII), wherein $R^{11}$ is hydrogen, by reaction with hydrogen bromide in acetic acid.

The following biological test methods, data and Examples serve to illustrate this invention. Test data for prizidilol (Example 2 of U.S. Pat. No. 4,053,601) are given as a reference.

Anti-hypertensive Activity

The anti-hypertensive activity of the compounds of the Examples was demonstrated by measuring the fall in blood pressure in anaesthetised rats. Compounds were dosed following dissolution in distilled water or in polyethylene glycol and dilution with 0.9% saline. The compounds were then administered intravenously. The blood pressure and heart rate were monitored directly, from a polythene cannula placed in the carotid artery. The doses required to lower blood pressure by 40 mm Hg, when administered intravenously, were obtained from a dose response graph.

| Compound of Example | µmol Kg$^{-1}$ |
|---|---|
| 11, as methanesulphonate | 2.1 |
| 1, as base | 8.0 |
| 1, as hydrochloride | 4.0 |
| 4, as methanesulphonate | 2.8 |
| 3, | 2.95 |
| 2, | 3.15 |
| Prizidilol | 14.0 |

Furthermore in anaesthetised cats, the compound of Example 1 as base and as hydrochloride at 4 and 7 µmol Kg$^{-1}$ respectively caused significant dose-dependent hypotension with minimal changes in aortic blood flow.

The anti-hypertensive activity of the compound of Example 1 (as base) and the compound of Example 4 (as methanesulphonate) was also demonstrated in conscious cats. Oral administration of these compounds at 19 µmol Kg$^{-1}$ and 16 µmol Kg$^{-1}$ respectively gave reductions in blood pressure with minimal changes in heart rate over a period of at least 2 hours.

The compound of Example 4 (as methanesulphonate) caused significant fails in blood pressure when administered intravenously at three dose levels from 3 to 13 µmol Kg$^{-1}$ to conscious spontaneously hypertensive rats. Oral administration of this compound at three doses from 25 to 102 µmol Kg$^{-1}$, produced a significant hypotensive effect. Both routes of administration caused prolonged, significant, reductions in blood pressure at up to and including 5 hours post dose.

Vasodilator Activity

The vasodilator activity of the compounds of the Examples was demonstrated by measuring the increase in blood flow in the autoperfused anaesthetised rat hindquarters (perfusion at constant pressure). The doses required to increase hindquarters blood flow by 50% were obtained.

| Compound of Example | Administration Mode | µmol Kg$^{-1}$ |
|---|---|---|
| 11, as methanesulphonate | intra-arterially | 1.1 |
| 1, as base | intravenously | 11.5 |
| 1, as hydrochloride | intravenously | 4.0 |
| 4, as methanesulphonate | intra-arterially | 1.7 |
| 3, | intravenously | 1.95 |
| 2, | intravenously | 1.43 |
| Prizidilol | intra-arterially | 10.00 |

The compound of Example 4 (as methanesulphonate) caused a prolonged duration of vasodilatation in this test method.

β-Adrenoceptor antagonist activity

The β-adrenoceptor antagonist acivity of the compounds of the Examples was demonstrated by measuring the inhibition of isoprenaline-induced tachycardia ($\beta_1$-receptors) in ganglion blocked anaesthetised cats. The doses required to inhibit isoprenaline-induced tachycardia by 50% (ID$_{50}$) were obtained after intravenous administration.

| Compound of Example | ID$_{50}$ (µmol Kg$^{-1}$) |
|---|---|
| 11, as methanesulphonate | 1.6 |
| 1, as base | 1.9 |

| Compound of Example | ID$_{50}$ (µmol Kg$^{-1}$) |
|---|---|
| 1, as hydrochloride | 4.3 |
| 4, as methanesulphonate | 1.4 |
| 3, | 7.84 |
| 2, | 8.63 |

In this test method the compound of Example 1 caused prolonged duration of inhibition; in comparison prizidilol, at doses giving a similar effect, gave a short duration of inhibition. In addition there was evidence that this compound has selectivity for $\beta_1$-receptors, unlike prizidilol. Thus this compound shows the desirable characteristic of cardiac selectivity in action.

From the above data it can be seen that the compounds of the Examples, and in particular the compound of Example 1 (as base, as hydrochloride and as methanesulphonate) and the compound of Example 11 cause prolonged hypotension and $\beta_1$-adrenoceptor antagonism over the same dose range. Thus they have a desirable profile of significant activity and have significantly advantageous duration. Furthermore they have minimal intrinsic sympathomimetic activity as shown by the absence of a tachycardia in spontaneously beating guinea pig right atria. The compound of Example 1 produced a maximal increase of approximately 10% of the maximal isoprenaline induced tachycardia in an anaesthetised ganglion blocked cat.

Bronchodilatation

The compound of Example 4 (as methanesulphonate) (at a bath concentration of 1 µg ml$^{-1}$) caused a 50% reduction in the spontaneous tone of an isolated intact guinea pig trachea, as assessed by the method of Coleman R. A. and Farmer J. B. (1971), J. Pharm. Pharmac., 23, 220–222, which was not inhibited by propanolol.

No toxic effcts were observed in the above tests, in particular no toxic effects were observed for the compound of Example 4 (as methanesulphonate) when administered orally to conscious spontaneously hypertensive rats at doses up to a maximum of 102 µmol Kg$^{-1}$.

EXAMPLE 1

6-[4-[3-[2-Hydroxy-3-[4-(2-(cyclopropylmethoxy)ethyl)-phenoxy[propylamino]propionamido]phenyl]-5-methyl-4,5-dihydro-3(2H)-pyridazinone (i) 6-[4-(3-Bromopropionamido)phenyl]-5-methyl-4,5-dihydro 3(2H)-pyridazinone A suspension of 6-(4-aminophenyl)-5-methyl-4,5-dihydro-3(2H)-pyridazinone (Curran et al., J. Med. Chem. 17, 273 (1974)) (75.0 g, 0.369 mol) and 3-bromoproionylchloride (100 g, 0.583 mol) in toluene (800 ml) was stirred under reflux for 16 hours. The reaction mixture was allowed to cool and the solid product collected, dried and stirred with water (500 ml) for 30 minutes. The crude product was collected, washed with water (500 ml) and dried to give 6-[4-(3-bromopropionamido)phenyl]-5-methyl-4,5-dihydro-3(2H)-pyridazinone (120 g, 97%), m.p. 215°–217° C.

This reaction can also be performed in acetonitrile at 70° C., under reflux, for 3 hours.

(ii) 6-[4-(3-Benzylaminopropionamido)phenyl]-5-methyl-4,5-dihydro-3(2H)-pyridazinone A suspension of 6-[4-(3-bromopropionamido)phenyl]-5-methyl-4,5-dihydro-3(2H)-pyridazinone (120 g, 0.355 mol) and benzylamine (152 g, 1.47 mol) in n-propanol (800 ml) was stirred under reflux for 16 hours. The reaction mixture was filtered whilst hot and white solid was collected, which was washed with ether to remove excess benzylamine. The crude material was boiled with ethanol (300 ml) for 2 hours; the mixture was cooled and filtered. The resulting white solid was washed with ether and dried to give 6-[4-(3-benzylaminopropionamido)phenyl]-5-methyl-4,5-dihydro-3(2H)-pyridazinone (114 g, 88%) as the hydrobromide salt m.p. 279°–285° C.

(iii) 6-[4-[3-[2-Hydroxy-3-[4-(2-(cyclopropylmethoxy)ethyl)-phenoxy]-N-benzylpropylamino]propionamido]phenyl]-5-methyl-4,5-dihydro-3(2H)-pyridazinone A mixture of 6-[4-(3-benzylaminopropionamido)-phenyl]-5-methyl-4,5-dihydro-3(2H)-pyridazinone (1.46 g, 0.004 mol), 1-[4-[2-(cyclopropylmethoxy)ethyl]-phenoxy]-2,3-epoxypropane (2.0 g, 0.008 mol) (British Pat. No. 1,515,978) and n-propanol was stirred and heated under reflux for 22 hours. Evaporation of the solvent under reduced pressure gave an oily residue which was purified by elution from a silica column with chloroform/methanol mixtures to give 6-[4-[3-[2-hydroxy-3-[4-(2-(cyclopropylmethoxy)ethyl]phenoxy]-N-benzylpropylamino]propionamido]phenyl]-5-methyl-4,5-dihydro-3(2H)-pyridazinone as a foam, 1.3 g, (38%); δ(CHCl₃) 0.18 and 0.53 (2m, 4H, cyclopropylmethylene protons), 1.23 (d, 3H, dihydropyridazinone 5-methyl) ppm.

(iv) 6-[4-[3-[2-Hydroxy-3-[4-(2-(cyclopropylmethoxy)ethyl)phenoxy]propylamino]propionamido]phenyl]-5-methyl-4,5-dihydro-3(2H)-pyridazinone A solution of the above amine (0.85 g, 0.00138 mol) in ethanol (60 ml) was agitated for 6 hours in a hydrogen atmosphere at 172 kPa (25 p.s.i.) in the presence of palladium hydroxide on carbon (0.3 g) as a catalyst. When hydrogen uptake ceased, the mixture was filtered and the solvent evaporated under reduced pressure to give a solid residue. Purification of the crude material was effected by elution from a silica column with chloroform/methanol mixtures to give the title compound as a white solid (0.3 g) in hydrate form, m.p. 54°–6° C.; δ(DMSO-d₆) 0.14, 0.44 and 0.97 (3m, 5H, cyclopropyl), 1.08 (d, 3H, dihydropyridazinone 5-methyl); γmax (mull) 3700–2300 (OH, NH), 1670 vs, broad (carbonyls), 1532, 1512 (amide)cm⁻¹.

The above material (obtained from another run) (2.7 g) was dissolved in ethanol (50 ml) and concentrated hydrochloric acid (0.6 ml) in ethanol (4 ml) was added. The solution was allowed to stand for 30 minutes, diethyl ether was added to the point of cloudiness, the solution was warmed until it became clear again and allowed to stand at room temperature to form a white precipitate. This was collected and dried to afford the title compound as the monohydrochloride (0.95 g); m.p. 145°–6° C.; δ(DMSO-d₆) 0.13, 0.43, 0.96 (3m, 5H, cyclopropyl), 1.07 (d, 3H, dihydropyridazinone). The analysis indicated about 0.5M H₂O.

EXAMPLE 2

6-[4-[3-[2-Hydroxy-3-[2-n-propyl-4-(2-(cyclopropylmethoxy)ethyl)phenoxy]propylamino]propionamido]-phenyl]-5-methyl-4,5-dihydro-3(2H)-pyridazinone (i) 2-(4-Allyloxyphenyl)ethanol 2-(4-Hydroxyphenyl)ethanol (100 g), anhydrous potassium carbonate (100 g) and allyl bromide (98 g) were refluxed with stirring for 17 hours. The mixture was cooled, filtered (washing through with acetone) and evaporated under reduced pressure to give an oily residue. This residue was dissolved in diethyl ether, washed with aqueous sodium hydroxide, washed with saturated brine, dried (MgSO₄) and evaporated in vacuo to afford an oil. This was chromatographed on a silica gel column using dichloromethane to afford 2-(4-allyloxyphenyl)ethanol (78 g).

(ii) 1-Allyloxy-4-[2-(cyclopropylmethoxy)ethyl]benzene

To a flask charged with redistilled dimethylsulphoxide (50 ml) and sodium hydride (50% dispersion, 4.8 g) was slowly added 2-(4-allyloxyphenyl)ethanol (17.8 g) at ice-bath temperature. Cyclopropylmethyl bromide (13.5 g) in dry dimethyl sulphoxide (20 ml) was added with cooling under nitrogen. The reaction mixture was stirred at room temperature overnight, poured on to ice-water and extracted into diethyl ether. The organic layer was thoroughly washed with saturated brine, evaporated under reduced pressure and chromatographed on silica using petroleum ether (40°–60°) as an eluant to afford 1-allyloxy-4-[2-(cyclopropylmethoxy)ethyl]benzene (9 g).

(iii) 2-Allyl-4-[2-(cyclopropylmethoxy)ethyl]phenol

The product from step (ii) (9.0 g) was stirred at 198° C. for 16 hours. The oily thermolysed product was chromatographed on a silica gel column using chloroform as eluant to give an oil 2-allyl-4-[2-cyclopropylmethoxy)ethyl]phenol (7.0 g).

(iv) 1-[2-Allyl-4-[2-(cyclopropylmethoxy)ethyl]phenoxy]-2,3-epoxypropane

The product from step (iii) (7.0 g), epibromohydrin (8.32 g) and anhydrous potassium carbonate (4.2 g) were stirred under reflux for 20 hours in dry methyl ethyl ketone (100 ml). The reaction mixture was cooled, filtered and the filtrate was evaporated under reduced pressure (removing excess epibromohydrin) to give 1-[2-allyl-4-[2-(cyclopropylmethoxy)ethyl]phenoxy]-2,3-epoxypropane as an oil (8.8 g).

(v) 6-[4-[3-[2-Hydroxy-3-[2-allyl-4-(2-(cyclopropylmethoxy)ethyl)phenoxy]-N-benzylpropylamino]propionamido]phenyl]-5-methyl-4,5-dihydro-3(2H)-pyridazinone A mixture of 6-[4-(3-benzylaminopropionamido)-phenyl]-5-methyl-4,5-dihydro-3(2H)-pyridazinone (5.5 g; 0.015 mol), 1-[2-allyl-4-[2-(cyclopropylmethoxy)ethyl]phenoxy]-2,3-epoxypropane (8.65 g; 0.03 mol) and n-propanol (100 ml) was stirred under reflux for 24 hours. The mixture was cooled, filtered and the filtrate was evaporated under reduced pressure and chromatographed on a silica gel column, using ethyl acetate as eluant, to give as a glass 6-[4-[3-[2-hydroxy-3-[2-allyl-4-(2-(cyclopropylmethoxy)ethyl)phenoxy]-N-benzylpropylamino]propionamido]phenyl]-5-methyl-4,5-dihydro-3(2H)-pyridazinone (4.4 g).

(vi) 6-[4-[3-[2-Hydroxy-3-[2-n-propyl-4-(2-(cyclopropylmethoxy)ethyl)phenoxy]propylamino]propionamido]phenyl]-5-methyl-4,5-dihydro-3(2H)-pyridazinone The product from step (v) (4.3 g) was dissolved in ethanol (100 ml) and hydrogenated at atmospheric pressure and at room temperature over (20%) palladium hydroxide on charcoal (Pearlman's catalyst) (1.5 g). After 3 hours further catalyst (0.5 g) was added and the mixture hydrogenated until no further hydrogen was taken up. The mixture was filtered and the filtrate was evaporated to dryness to give a residue (3.5 g). This was chromatographed on a silica gel column (high pressure liquid chromatography) using as eluant dichloromethane (20):methanol (1):acetonitrile (trace) to give the title compound which formed a glass (1.65 g) under diethyl ether; δ(DMSO-d₆) 0.14, 0.44 and 0.97 (3m, 5H, cyclopropyl), 1.08 (d, 3H, 5-methyl) ppm; γmax (1% KBr disc) 3700–2100 (OH, NH), 1670 (vs, broad, carbonyls), 1535 (vs, amide)cm⁻¹.

EXAMPLE 3

6-[4-[3-[2-Hydroxy-3-[2-methyl-4-(2-(cyclopropylmethoxy)ethyl)phenoxy]propylamino]propionamido]phenyl]-5-methyl-4,5-dihydro-3(2H)-pyridazinone (i) 2-(4-Benzyloxy-3-methylphenyl)ethanol 2-(4-Hydroxy-3-methylphenyl)ethanol (18 g), benzyl chloride (15.4 g) and anhydrous potassium carbonate (90 g) were stirred under reflux in methyl ethyl ketone (500 ml) for 20 hours. The reaction mixture was cooled and evaporated under reduced pressure to give an oily residue. This residue was dissolved in dichloromethane, washed with 2N sodium hydroxide (2×), washed with brine (2×), dried (MgSO₄), and evaporated under reduced pressure to give an oil. This was triturated under petroleum ether (40°–60°) (200 ml) with cooling to afford 2-(4-benzyloxy-3-methylphenyl)ethanol as a white solid (26.0 g).

(ii) 1-Benzyloxy-2-methyl-4-[2-(cyclopropylmethoxy)ethyl]-benzene

To a flask charged with redistilled dimethylsulphoxide (100 ml) and sodium hydride (50% dispersion, 4.28 g), at 60°–65° C. was added 2-(4-benzyloxy-3-methylphenyl)ethanol (18.0 g) followed by the dropwise addition of cyclopropylmethyl bromide (12.04 g). The reaction mixture was stirred at about 75° C. for 48 hours, poured on to ice-water (1000 ml) and extracted with vigorous stirring into diethyl ether (1000 ml). The ether layer was dried (MgSO₄) and evaporated under reduced pressure to afford an oily residue. This residue was chromatographed on preparative high pressure liquid chromatography using petroleum ether (40°–60°) and petroleum ether/diethyl ether (5:1) as eluants. The desired fractions were collected and evaporated under reduced pressure to give 1-benzyloxy-2-methyl-4-[2-(cyclopropylmethoxy)ethyl]-benzene (13.0 g) as an oil.

(iii) 1-Hydroxy-2-methyl-4-[2-cyclopropylmethoxy)ethyl]-benzene

1-Benzyloxy-2-methyl-4-[2-(cyclopropylmethoxy)ethyl]-benzene (13.0 g) in ethanol (100 ml) was hydrogenated for 4 hours, on a Parr apparatus, in the presence of palladium hydroxide on charcoal (20%; 3.0 g). The reaction mixture was filtered and evaporated to afford 1-hydroxy-2-methyl-4-[2-cyclopropylmethoxy)ethyl]-benzene (8.6 g) as an oil.

(iv) 1-[2-Methyl-4-[2-(cyclopropylmethoxy)ethyl]-phenoxy]-2,3-epoxypropane

1-Hydroxy-2-methyl-4-[2-cyclopropylmethoxy)ethyl]-benzene (8.5 g), epibromohydrin (22.4 g) and anhydrous potassium carbonate (22.5 g) were stirred under reflux for 60 hours in dry methyl ethyl ketone (200 ml). The reaction mixture was cooled, filtered and evaporated under reduced pressure (removing excess epibromohydrin) to give 1-[2-methyl-4-[2-(cyclopropylmethoxy)ethyl]phenoxy]-2,3-epoxypropane (10.5 g) as an oil.

(v) 6-[4-[3-[2-Hydroxy-3-[2-methyl-4-(2-(cyclopropylmethoxy)ethyl)phenoxy]-N-benzylpropylamino]propionamido]phenyl]-5-methyl-4,5-dihydro-3(2H)-pyridazinone 6-[4-(3-Benzylaminopropionamido)phenyl]-5-methyl-4,5-dihydro-3(2H)-pyridazinone (7.0 g; 0.019 mol) and 1-[2-methyl-4-[2-(cyclopropylmethoxy)ethyl]phenoxy]-2,3-epoxypropane (7.32 g; 0.028 mol) were stirred under reflux in n-propanol (200 ml) for 17 hours. n-Propanol (100 ml) was distilled off and the mixture subjected to reflux for a further 24 hours. The reaction mixture was cooled, filtered and evaporated under reduced pressure to give an oily residue. This was subjected to high pressure liquid chromatography with dichloromethane:acetonitrile:methanol (200:4:4) as eluant. The fractions containing the desired compound were collected and evaporated under reduced pressure to give 6-[4-[3-[2-hydroxy-3-[2-methyl-4-(2-(cyclopropylmethoxy)ethyl)phenoxy]-N-benzylpropylamino]propionamido]phenyl]-5-methyl-4,5-dihydro-3(2H)-pyridazinone (5.2 g) as an oil. Unreacted epoxide (3.6 g) was also recovered.

(v) 6-[4-[3-[2-Hydroxy-3-[2-methyl-4-(2-(cyclopropylmethoxy)ethyl)phenoxy]propylamino]propionamido]phenyl]-5-methyl-4,5-dihydro-3(2H)-pyridazinone The product from part (v) above (5.0 g) in ethanol (100 ml) was hydrogenated on a Parr apparatus for 3 hours in the presence of palladium hydroxide on charcoal (20%, 1.5 g). The reaction mixture was filtered through diatomaceous earth and evaporated under reduced pressure to afford an oil. This was chromatographed using high pressure liquid chromatography using dichloromethane/methanol (10:1) as eluant to give 6-[4-[3-[2-hydroxy-3-[2-methyl-4-(2-(cyclopropylmethoxy)ethyl)phenoxy]propylamino]propionamido]phenyl]-5-methyl-4,5-dihydro-3(2H)-pyridazinone (2.35 g); δ(DMSO-d₆) 0.15, 0.45, 0.98 (3m, 5H, cyclopropyl), 1.08 (d, 3H, 5-methyl), 2.15 (s, 3H, methyl) ppm.

EXAMPLE 4

6-[4-[3-[2-Hydroxy-3-[4-(2-(cyclopropylmethoxy)ethyl)phenoxy]propylamino]propionamido]phenyl]-5-methyl-4,5-dihydro-3(2H)-pyridazinone In a manner similar to that of Example 1 (iv), 6-[4-[3-[2-hydroxy-3-[4-(2-(cyclopropylmethoxy)ethyl)phenoxy]-N-benzylpropylamino]propionamido]phenyl]-5-methyl-4,5-dihydro-3(2H)-pyridazinone (22 g) in ethanol (350 ml) was agitated for 5 hours in a hydrogen atmosphere at 344 kPa (50 p.s.i.) in the presence of palladium hydroxide on charcoal (5 g). The catalyst was removed by filtration and solvent removed under reduced pressure to afford the title compound as a yellow foam (15 g). To a solution of this in dichloromethane (800 ml) was added a solution of methanesulphonic acid (8.60 g) in dichloromethane (100 ml) with stirring. The mixture was evaporated under reduced pressure to give a yellow solid which was crystallised from isopropanol/ethanol (50:50; 400 ml) to yield the title compound as the monomethanesulphonate salt (16 g), m.p. 185°–6° C. Conversion of this material (from another run) by base formation and retreatment with methanesulphonic acid afforded material with m.p. 186°–7° C.

EXAMPLE 5

6-[4-[3-[2-Hydroxy-3-[4-(2-(cyclopropylmethoxy)ethyl)phenoxy]propylamino]propionamido]phenyl]-5-methyl-4,5-dihydro-3(2H)-pyridazinone (i) 1-[4-(2-Cyclopropylmethoxyethyl)phenoxy]-2,3-epoxypropane (150 g) in methanol (300 ml) was added to a stirred mixture of 0.91 ammonia in methanol (25%; 2.25 L). The reaction mixture was stirred overnight at room temperature, filtered and the filtrate evaporated under reduced pressure. The resultant solid was dissolved in (hot n-propanol 200 ml) and diethyl ether added to the point of turbidity. On cooling white crystals were collected to give 3-[4-(2-(cyclopropylmethoxy)ethyl)phenoxy]-2-hydroxypropylamine (94 g), m.p. 79°–80° C. (recrystallised from acetonitrile).

In an alternative method, N-benzyl-3-[4-[2-cyclopropylmethoxy)ethyl]phenoxy]-2-hydroxypropylamine (1.90 g) (see Example 6 i) in ethanol (50 ml) was hydrogenated at 344 kPa (50 p.s.i.) in the presence of palladium hydroxide on carbon (0.5 g). The mixture was filtered and the filtrate evaporated to give a colourless oil which crystallised on standing. This was slurried with petroleum ether (40°–60°) and filtered to give 3-[4-(2-(cyclopropylmethoxy)ethyl)phenoxy]-2-hydroxypropylamine (1.14 g) as a white crystalline solid, identical with authentic material by chromatography and a nuclear magnetic resonance spectrum.

(ii) Part of the product from (i) (48 g), 6-[4-(3-bromopropionamido)phenyl]-5-methyl-4,5-dihydro-3(2H)-pyridazinone (60 g) and triethylamine (36 g) were stirred under reflux in n-propanol (700 ml) for 18 hours. The reaction mixture was cooled and evaporated under reduced pressure to afford an oil. This oil was subjected to column chromatography on silica using dichloromethane/methanol (gradient elution 100:0 to 100:5). The desired fractions were combined and purified on another silica column (eluting with ethyl acetate/methanol/ammonia 100:20:0.5). The desired fractions were combined and evaporated under reduced pressure to form the title compound (30 g). Part of this was converted to the methanesulphonate salt as in Example 4.

The above reaction was performed in analogous manner using n-propylamine as base. The reaction was also repeated in the absence of base but lower yields were obtained.

EXAMPLE 6

6-[4-[3-[2-Hydroxy-3-[4-(2-(cyclopropylmethoxy)ethyl)phenoxy]propylamino]propionamido]phenyl]-5-methyl-4,5-dihydro-3(2H)-pyridazinone (i) 1-[4-(2-Cyclopropylmethoxyethyl)phenoxy]-2,3-epoxypropane (10 g) and benzylamine (13 g) were stirred under reflux, in n-propanol (100 ml) for 20 hours. The mixture was cooled and evaporated under reduced pressure to give a residue. This was stirred under petroleum ether (60°–80°) for 30 minutes; the solvent was decanted and the residue triturated with further petroleum ether. A white solid was obtained, collected by filtration and recrystallised from acetonitrile to afford N-benzyl-3-[4-(2-(cyclopropylmethoxy)ethyl)phenoxy]-2-hydroxypropylamine (8.8 g), m.p. 75°–6° C.

In an alternative method, 3-[4-(2-(cyclopropylmethoxy)ethyl)phenoxy]-2-hydroxypropylamine (1.33 g), (see Example 5 (i) in ethanol (20 ml) was stirred at room temperature whilst a solution of benzaldehyde (1.06 g) in ethanol (20 ml) was added. The mixture was poured on to a slurry of 5% palladium on charcoal (0.5 g) in ethanol (5 ml) and hydrogenated at 344 kPa (50 p.s.i.) for 10 minutes. The mixture was filtered through diatomaceous earth and the filtrate evaporated to give a clear oil which crystallised on standing to give N-benzyl-3-[4-[2-(cyclopropylmethoxy)ethyl]phenoxy]-2-hydroxypropylamine, in quantitative yield, identical to an authentic sample by chromatography and a nuclear magnetic resonance spectrum.

In yet a further method, N-benzyl-3-[4-[2-(cyclopropylmethoxy)ethyl]phenoxy]-2-hydroxypropylamine was formed in the following manner. D,L-Glyceraldehyde (5.0 g) was added to benzylamine (18.19 g) in methanol (90 ml) and the mixture was hydrogenated at 344 kPa (50 p.s.i.) over 5% palladium on carbon (1.0 g) for 3½ hours. The mixture was filtered, evaporated under reduced pressure and subjected to column chromatography on silica (eluant dichloromethane:methanol saturated with ammonia 9:1) to give as an oil 3-benzylamino-1,2-propanediol (5.4 g). Part of this (4.9 g) and benzaldehyde (10 ml) were heated to 150° C. for 30 minutes. Volatiles including water were collected by distillation. The mixture was then cooled, benzaldehyde distilled off at low pressure, and the desired product 2-phenyl-3-benzyl-5-hydroxymethyloxazolidine (2.7 g) distilled at 190° C. (0.2 mm Hg). To this oil (2.69 g) in pyridine (4 ml) was added in portions toluene-p-sulphonyl chloride (1.90 g) at 5° C. The mixture was stirred at room temperature for 2 hours, treated with potassium carbonate (1.65 g) in water (7.5 ml), extracted into dichloromethane (3×10 ml) and evaporated under reduced pressure to give an oil. This oil dissolved in dimethylformamide (5 ml) was added in portions, to a solution of the anion of 4-[2-(cyclopropylmethoxy)ethyl]phenol (1.9 g) (prepared in situ using sodium hydride (0.5 g)) in dimethylformamide (5 ml) at 5° C. The mixture was heated for 6 hours to 60°–70° C., cooled, poured on to ice (30 g), extracted into diethyl ether (3×30 ml) and evaporated under reduced pressure to give an oil. This was slurried under water (30 ml), concentrated hydrochloric acid (6 ml) was added, stirred for 30 minutes and ether (30 ml) added. The resultant solid (1.1 g) was filtered off, slurried with ether, filtered and separated between dichloromethane and dilute sodium hydroxide. The dichloromethane layer was dried, filtered and evaporated to give an oil which crystallised on standing to afford N-benzyl-3-[4-[2-(cyclopropylmethoxy)ethyl]phenoxy]-2-hydroxypropylamine (0.8 g), identical with an authentic sample by chromatography and a nuclear magnetic resonance spectrum.

(ii) Part of compound of (i) above (1.0 g) 6-[4-(3-bromopropionamido)phenyl]-5-methyl-4,5-dihydro-3(2H)-pyridazinone (1.3 g) and triethylamine (1 ml) were stirred, in ethanol (20 ml), under reflux for 60 hours. The reaction mixture was cooled and evaporated under reduced pressure to give an oil. This oil was dissolved in dichloromethane (25 ml), washed with dilute ammonia (2×20 ml), dried over sodium sulphate, filtered, and evaporated under reduced pressure to give 6-[4-[3-[2-hydroxy-3-[4-(2-(cyclopropylmethoxy)ethyl)-phenoxy]-N-benzylpropylamino]propionamido]phenyl-5-methyl-4,5-dihydro-3(2H)-pyridazinone. This was dissolved in n-propanol (15 ml) with warming; solid fumaric acid (0.35 g) was added with warming and the solution allowed to cool to yield the hemifumarate salt (1.3 g), m.p. 124°–7° C.

This reaction was performed in analogous manner using tri-n-propylamine in n-propanol, under reflux.

(iii) Hydrogenation was performed in a manner similar to Example 7(b).

EXAMPLE 7

6-[4-[3-[2-Hydroxy-3-[4-(2-(cyclopropylmethoxy)ethyl)phenoxy]propylamino]propionamido]phenyl]-5-methyl-4,5-dihydro-3(2H)-pyridazinone (i) In a manner similar to that of Example 1 (iii), 6-[4-(3-benzylaminopropionamido)phenyl]-5-methyl-4,5-dihydro-3(2H)-pyridazinone (21.8 g) and 1-[4-(2-cyclopropylmethoxyethyl)phenoxy]-2,3-epoxypropane (19.4 g) in n-propanol (200 ml) were stirred under reflux for 4½ hours. The mixture was cooled and a solution of fumaric acid (6.96 g) in hot n-propanol (150 ml) added with stirring. Cooling (and seeding) and stirring overnight afforded 6-[4-[3-[2-hydroxy-3-[4-(2-(cyclopropylmethoxy)ethyl)phenoxy]-N-benzylpropylamino]propionamido]phenyl]-5-methyl-4,5-dihydro-3(2H)-pyridazinone hemifumarate (31.05 g), m.p. 125°–8° C.

In an alternative method, 6-(p-propenoylaminophenyl)-4,5-dihydro-5-methyl-3(2H)-pyridazinone (1.0 g) (DE-A No. 3209158) and N-benzyl-3-[4-(2-(cyclopropylmethoxy)ethyl)phenoxy]-2-hydroxypropylamine (1.0 g) in n-propanol (15 ml) were heated under reflux for 32 hours. The reaction mixture was cooled and filtered and to the filtrate was added fumaric acid (0.33 g) in n-propanol (5 ml). The mixture was stirred, seeded and overnight a solid formed; this was collected to give the above named hemifumarate (1.3 g), m.p. 124°–8° C.

(ii) The above hemifumarate salt was subjected to catalytic hydrogenation under a variety of conditions:

- (a) Hemifumarate (0.728 g) in methanol (20 ml) was hydrogenated over 10% Pd/C (wet with 45% water) (0.1 g) for 4 hours at 344 kPa (50 p.s.i.). The reaction mixture was filtered, the filtrate evaporated to low volume and mixed with dichloromethane (15 ml)/0.5M sodium hydroxide (20 ml)/methanol (10 ml). The emulsified organic layer was collected and the aqueous layer washed with dichloromethane. The combined organic layers were washed with water, dried, filtered and evaporated under reduced pressure to afford the title compound (0.48 g). This was converted to the methanesulphonate salt (0.38 g) on treatment with methanesulphonic acid in acetonitrile.
- (b) To a stirred mixture of hemifumarate (3.64 g) and 10% Pd/C (0.18 g) in ethanol (35 ml) was added hydrazine hydrate (1.94 ml). The reaction mixture was stirred at room temperature for 22 hours, filtered and evaporated to give an oil. This was mixed with dichloromethane (50 ml/1M sodium bicarbonate (20 ml)/water (20 ml) to give an emulsion which was cleared with salt. The organic layer was collected, washed with water, dried, filtered and evaporated under reduced pressure to give the title compound as an oil (2.36 g). This was converted to the methanesulphonate salt (1.48 g) on treatment with methanesulphonic acid in acetonitrile.
- (c) Hemifumarate (0.36 g), 10% Pd/C (0.03 g) formic acid (0.5 ml), water (0.5 ml) and methanol (5 ml) were stirred at room temperature for 16 hours. Thin layer chromatography indicated the presence of the title compound.

EXAMPLE 8

(+) and (−)-6-(4-Aminophenyl)-5-methyl-4,5-dihydro-3(2H)-pyridazinone

Racemic 6-(4-aminophenyl)-5-methyl-4,5-dihydro-3(2H)-pyridazinone (2.0 g) dissolved in a mixture of acetonitrile (80 ml) and dichloromethane (30 ml) was added to a column of ionically bound (R)-N-(3,5-dinitrobenzoyl)phenyl)glycine on 40 μm γ-aminopropyl silanized silica (2.1 kg), packed at 1794 kPa (260 p.s.i.) (by slurrying with dichloromethane (1.5 L)) in a Jobin-Yvon medium pressure liquid chromatography system. The column was eluted with dichloromethane/methanol (199:1) over 9 hours at a rate of 80 ml min$^{-1}$. Detection was by u.v. at 280 nm. A broad peak was obtained from which fractions were collected.

The earlier fractions were enriched (−)-enantiomer. These fractions were combined and re-chromatographed through the same column with the same eluant. This afforded (−)-enantiomer (1.2 g) in approximately 100% enantiomeric excess.

The selected column fractions were evaporated, triturated with diethyl ether, filtered and the resultant solid washed with diethyl ether and dried at 80° C. for 18 hours to give (−)-6-(4-aminophenyl)-5-methyl-4,5-dihydro-3(2H)-pyridazinone, m.p. 203°–4° C.; $[\alpha]_D^{25} = -399°$ [concentration 0.74% in ethanol:water:conc. HCl (17:2:1)].

The later fractions from the first column were enriched (−)-enantiomer (approximately 75% enrichment). This (0.05 g) was subjected to high pressure liquid chromatography (Jobin-Yvon system) over a column of ionically bound (S)-N-(3,5-dinitrobenzoyl)-phenylglycine on 25–40 μm γ-aminopropyl silanized silica (55 g) eluting with dichloromethane/methanol (199:1). The appropriate fractions were combined with fractions from another run and re-chromatographed through the same column. This afforded (+)-enantiomer (0.035 g) in approximately 100% enantiomeric excess.

The selected column fractions were evaporated, triturated with diethyl ether, filtered and the resultant solid washed with diethyl ether and dried at 80° C. for 18 hours to give (+)-6-(4-aminophenyl)-5-methyl-4,5-dihydro-3(2H)-pyridazinone, m.p. 206°–8° C.; $[\alpha]_D^{25} = +376°$ [concentration 0.74% in ethanol:water:conc. HCl (17:2:1)].

EXAMPLE 9

(−)-6-[4-(3-Bromopropionamido)phenyl]-5-methyl-4,5-dihydro-3(2H)-pyridazinone (−)-6-(4-Aminophenyl)-5-methyl-4,5-dihydro-3(2H)-pyridazinone (0.195 g) suspended in dichloromethane (15 ml) was cooled to 0° C. Aqueous saturated sodium bicarbonate (15 ml) was added to form a two phase system. To the organic phase was added with stirring 3-bromopropionyl chloride (0.248 g) in dichloromethane (5 ml). The mixture was allowed to warm to room temperature and vigorously stirred for 3 hours to give a fine suspension. This was filtered to give the title compound (0.279 g); $[\alpha]_D^{25} = -333°$ [concentration 0.91% in dimethylformamide]: nuclear magnetic resonance spectrum consistent with racemic material. Material from another run gave C, 49.41%; H, 4.73%; H, 12.22%; Br, 23.14%: theory C, 49.72%, H, 4.77%; N, 12.43%; Br, 23.63%.

EXAMPLE 10

(+) and (−)-3-[4-(2-(Cyclopropylmethoxy)ethyl)phenoxy]-2-hydroxypropylamine (i) by resolution (±)-3-[4-(2-(Cyclopropylmethoxy)ethyl)phenoxy]-2-hydroxypropylamine (25 g) was dissolved in hot water (200 ml) and methanol (50 ml). To this solution was added, with vigorous stirring, a solution of L-(+)-mandelic acid (14.35 g) in hot water (200 ml). The mixture was stirred for five minutes, cooled and seeded to give crystals. These were collected and recrystallised three times from hot water to afford a mandelate salt of 3-[4-(2-(cyclopropylmethoxy)ethyl)phenoxy]-2-hydroxypropylamine (5.04 g). To part of this compound (4.54 g) in chloroform (75 ml) was added 15% sodium carbonate solution (75 ml) and the two phase mixture was vigorously stirred at room temperature for one hour. The two layers were separated, the aqueous layer washed with chloroform (3×25 ml) and the organic layer and chloroform washings were combined, dried and evaporated under reduced pressure to give a residue (2.81 g). This residue was dissolved in hot acetonitrile (25 ml), filtered, evaporated to low volume and cooled to afford (−)-3-[4-(2-(cyclopropylmethoxy)ethyl)phenoxy]-2-hydroxypropylamine (2.05 g), $[\alpha]_D^{25} = -17.77°$ [concentration 1.1% in ethanol:water:concentrated HCl (17:2:1)]: nuclear magnetic resonance spectrum consistent with racemic material; identical by chromatography.

(±)-3-[4-(2-(Cyclopropylmethoxy)ethyl)phenoxy]-2-hydroxy-propylamine (30 g) was dissolved in hot ethanol (350 ml). To this was added dibenzoyl-1-tartaric acid (21.27 g) dissolved in hot ethanol (300 ml). This mixture was stirred for 30 minutes, cooled and a white crystalline solid was collected. This was recrystallised three times from methanol/ethanol mixtures to afford a dibenzoyl-1-tartrate salt of 3-[4-(2-(cyclopropylmethoxy)ethyl)-phenoxy]-2-hydroxypropylamine (15.56 g). To this material (combined with some from another run) (19 g) in chloroform (200 ml) was added 15% sodium carbonate (200 ml) and the two phase mixture was vigorously stirred at room temperature. The two layers were separated, the aqueous layer washed with chloroform (3×25 ml) and the organic layer and chloroform washings were combined, washed with aqueous sodium bicarbonate, washed with water, dried and evaporated under reduced pressure to give a white solid. This was dissolved in methanol, filtered, evaporated under reduced pressure, slurried with petroleum ether (40°–60°) and filtered to give (+)-3-[4-(2-(cyclopropylmethoxy)ethyl)phenoxy]-2-hydroxypropylamine (10.61 g), $[\alpha]_D^{25} = +17.95°$ [concentration 1.13% in ethanol:water:concentrated HCl (17:2:1)]: nuclear magnetic resonance spectrum consistent with racemic material; identical by chromatography.

(ii) by synthesis

To a stirred suspension of mannitol diacetonide (26.2 g) in benzene (800 ml) was added lead tetraacetate (44.2 g) over 5 minutes. The resultant solid was broken up to give a cloudy solution, stirred for 45 minutes, filtered, evaporated under reduced pressure and distilled to give as an oil, acetone-d-glyceraldehyde (17.7 g), b.p. 44°–8° C./11 mm Hg. To a solution of this in methanol (60 ml), at 5° C., was added slowly a solution of benzylamine (10.7 g) in methanol (60 ml). This mixture was added to a slurry of 5% palladium on carbon (1.5 g) in methanol (40 ml) and hydrogenated at 344 KPa (50 p.s.i.) for 30 minutes. The mixture was filtered, treated with 6N hydrochloric acid (150 ml), distilled until the vapour temperature was 98° C. and heated under reflux for one hour. The mixture was cooled, taken to pH 14 with sodium hydroxide, extracted into dichloromethane (3 times), dried and evaporated under reduced pressure to give an oil. This oil was extracted with boiling ether (twice), filtered whilst warm and on standing gave as a crystalline solid (S)-(−)-3-benzylamino-1,2-propanediol (10.1 g), $[\alpha]_D^{25} = -25.72°$ [concentration 1.01% in ethanol:water:concentrated HCl (17:2:1)], m.p. 63° C.

Part of this (7.24 g) in warm toluene (35 ml) and benzaldehyde (4.66 g) were stirred at room temperature for 90 minutes, then stirred under reflux for 60 minutes removing water using a Dean-Stark apparatus. The solution was then cooled, evaporated under reduced pressure to give an oil which was crystallised from ethyl acetate to give (S)-(−)-2-phenyl-3-benzyl-5-hydroxymethyloxazolidine (8.1 g), m.p. 100° C.

Part of this (6.73 g) in pyridine (10 ml) and toluene-p-sulphonyl chloride (4.8 g) were stirred at room temperature for 2 hours (initial cooling). Potassium carbonate (4.13 g) in water (20 ml) was added cautiously and the product extracted into dichloromethane (3 times). The organic extracts were dried and evaporated under reduced pressure to give the tosylate (10.7 g) as an oil. The tosylate in dimethylformamide (12.5 ml) was added in portions to a solution of the anion of 4-(2-(cyclopropylmethoxy)ethyl)phenol (4.8 g) (formed from sodium hydride (50% dispersion; 1.25 g)) in dimethylformamide (12.5 ml). The reaction mixture was heated at 70° C. for 6 hours, poured on to ice (90 g) and extracted into ether (3 times). The ether extracts were washed with water, dried and evaporated to give (S)-(−)-2-phenyl-3-benzyl-5-(4-(2-cyclopropylmethylmethoxy)ethyl)phenoxymethyl)oxazolidine as an orange oil (9.78 g).

This oxazolidine was slurried in a mixture of water (80 ml) and concentrated hydrochloric acid (20 ml) for one hour until the orange oil had changed to a pale yellow solid. The solid was filtered, washed with water, slurried with ether, filtered and dried under vacuum to give (S)-(−)-2-hydroxy-3-[4-(2-(cyclopropylmethoxy)ethyl)phenoxy]-N-benzylpropylamine as a hydrochloride (5.18 g), m.p. 172° C. (recrystallisation from acetonitrile), $[\alpha]_D^{25} = -14.0°$ [concentration 1.11% in ethanol:water:concentrated HCl (17:2:1)], m.p. 172° C.

Part of this (0.3 g) in ethanol (20 ml) was hydrogenated at 344 KPa (50 p.s.i.), in the presence of palladium hydroxide on carbon (0.1 g), for 4 hours at room temperature. The mixture was filtered, evaporated under reduced pressure and the resultant solid slurried with petroleum ether (40°–60°) (40 ml) and filtered to give the (−)-isomer of the title compound (0.15 g), $[\alpha]_D^{25} = -16.26°$ [concentration 1.11% in ethanol:water:concentrated HCl (17:2:1)]; nuclear magnetic resonance spectrum consistent with racemic materials; identical by chromatography. This intermediate is a further aspect of the present invention.

EXAMPLE 11

(−)-6-[4-[3-[2-(−)-Hydroxy-3-[4-(2-(cyclopropylmethoxy)ethyl)phenoxy]propylamino]propionamido]phenyl]-5-methyl-4,5-dihydro-3(2H)-pyridazione[(−)(−)isomer]

(−)-3-[4-(2-(Cyclopropylmethoxy)ethyl)phenoxy]-2-hydroxypropylamine (0.177 g) and triethylamine (0.144 g) in anhydrous n-propanol (25 ml) were stirred under reflux. To this mixture was added, in portions, (−)-6-[4-(3-bromopropionamido)phenyl]-5-methyl-4,5-dihydro-3(2H)-pyridazinone (0.240 g) suspended in n-propanol (5 ml). The reaction mixture was stirred under reflux for a further 5 hours, cooled and evaporated under reduced pressure with adsorption on to silica (3.0 g). This was then subjected to column chromatography eluting firstly with dichloromethane/methanol (20:1) and subsequently with dichloromethane/33% methylamine in ethanol (30:1). The desired fractions were combined and evaporated under reduced pressure to afford the title compound (0.200 g); $[\alpha]_D^{25} = -197°$ [concentration 0.73% in ethanol:water:conc. HCl (17:2:1)]: nuclear magnetic resonance spectrum consistent with racemic material. Found: C, 65.10%; H, 7.45%; N, 10.51%: Theory: C, 66.65%; H, 7.33%; N, 10.72%: contains a little water. A portion of this was converted to the mesylate salt $[\alpha]_D^{25} = -169°$ [concentration 0.92% in ethanol:water:conc. HCl (17:2:1)]: nuclear magnetic resonance spectrum consistent with racemic material. Found: C, 57.81%; H, 6.97%; N, 9.05% Theory: C, 58.24%; H, 6.84%; N, 9.05%.

EXAMPLE 12

(−)-6-[4-[3-[2-(+)-Hydroxy-3-[4-(2-cyclopropylmethoxy)ethyl)phenoxy]propylamino]propionamido]-phenyl]-5-methyl-4,5-dihydro-3(2H)-pyridazinone[(−)(+)isomer]

In a manner similar to that of Example 11, (−)-6-[4-(3-bromopropionamido)phenyl]-5-methyl-4,5-dihydro-3(2H)-pyridazinone (1.60 g) and (+)-3-[4-(2-cyclopropylmethoxyethyl)phenoxy]-2-hydroxypropylamine (1.50 g) gave the title compound which was converted to the mesylate salt (1.92 g); $[\alpha]_D^{25} = -140°$ [concentration 1.08% in ethanol:water:conc. HCl (17:2:1)]; nuclear magnetic resonance spectrum consistent with racemic material.

EXAMPLE 13

6-[4-[3-[2-Hydroxy-3-[4-(2-(cyclopropylmethoxy)ethyl)phenoxy]propylamino]propionamido]phenyl]-5-methyl-4,5-dihydro-3(2H)-pyridazinone A suspension of 6-(4-aminophenyl)-5-methyl-4,5-dihydro-3(2H)-pyridazinone (5.0 g) in tetrahydrofuran (50 ml) was stirred and treated with β-alanoylchloride hydrochloride (3.99 g) in small portions. The resultant mixture was stirred at 50° C. for 30 hours and a further portion of β-alanoylchloride hydrochloride (0.4 g) was added. A third portion of β-alanoylchloride hydrochloride (0.2 g) was added after a further 17 hours. After a total reaction time of 56 hours the reaction mixture was cooled to ambient temperature, and added to water (80 ml). The aqueous solution was basified to pH 12 with 1M sodium hydroxide (approximately 50 ml), and a white solid crystallised from the aqueous solution. The product was filtered under reduced pressure, washed with water (10 ml), then dried in a vacuum dessicator over phosphorus pentoxide to give 6-[4-(3-aminopropionamido)phenyl]-5-methyl-4,5-dihydro-3(2H)-pyridazinone (4.6 g), m.p. 210°–213° C. (recrystallised from methanol). This material and 1-[4-(2-(cyclopropylmethoxy)ethyl]phenoxy]-2,3-epoxypropane were heated at 100° C. in dimethylformamide to give a reaction mixture containing the title compound as indicated by thin layer chromatography.

EXAMPLE 14

A tablet for oral administration is prepared by combining:

| | Mg/Tablet | |
|---|---|---|
| The compound of Example 4 (as methanesulphonate) | 118.9 | (equivalent to 100 mg free base) |
| Maize Starch | 30.0 | |
| Povidone 30 | 10.0 | |
| Microcrystalline Cellulose | 64.1 | |
| Calcium Carboxymethyl Starch | 25.0 | |
| Magnesium Stearate | 2.0 | |
| | 250.0 | | into a 9 mm diameter tablet.

EXAMPLE 15

A capsule for oral administration is prepared by combining:

| | Mg/Capsule | |
|---|---|---|
| The compound of Example 4 (as methanesulphonate) | 118.9 | (equivalent to 100 mg free base) |
| Pregelatinised Starch | 60.0 | |
| Calcium Carboxymethyl Starch | 19.0 | |
| Magnesium Stearate | 2.0 | |
| | 200.0 | |

The formulation is filled in a size 2 hard shell gelatin capsule.

EXAMPLE 16

An injection for parenteral administration is prepared by combining:

| | % w/v | |
|---|---|---|
| The compound of Example 4 (as methanesulphonate) | 1.7 | (equivalent to 15 mg/ml free base) |
| Dextrose | 2.0 | |
| Water for injection | 100.0 | |
| Magnesium Stearate | 2.0 | |
| | 200.0 | |

The formulation is filled into 2 and 5 ml ampoules or vials.

What is claimed is:

1. A compound of the formula (I):

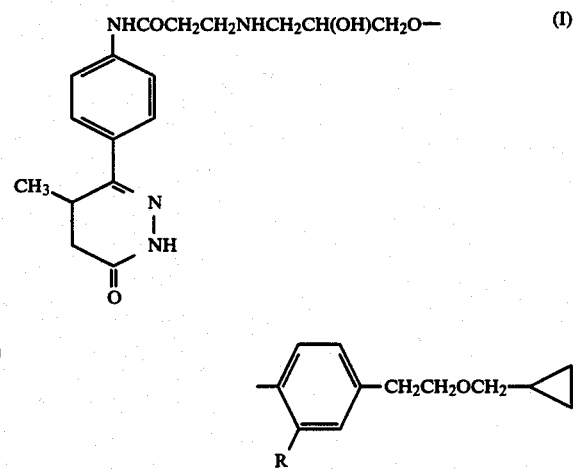

or a pharmaceutically acceptable salt thereof, wherein R is hydrogen or $C_{1-4}$alkyl.

2. A compound according to claim 1 which is:

6-[4-[3-[2-hydroxy-3-[4-(2-(cyclopropylmethoxy)ethyl)-phenoxy]propylamino]propionamido]phenyl]-5-methyl-4,5-dihydro-3(2H)-pyridazinone.

3. A compound according to claim 1 which is: 6-[4-[3-[2-hydroxy-3-[4-(2-(cyclopropylmethoxy)ethyl)-phenoxy]propylamino]propionamido]phenyl]-5-methyl-4,5-dihydro-3(2H)-pyridazinone methanesulphonate.

4. A racemic or diastereoisomeric mixture of a compound according to any one of claims 1 to 3.

5. A racemic or diastereoisomeric mixture of a compound according to any one of claims 1 to 3 which includes the (−) (−)isomer.

6. A compound according to any one of claims 1 to 3 which comprises the (−) (−)isomer substantially free of the (−) (+), (+) (−) and (+) (+)isomers.

7. A compound according to claim 1 which is (−)-6-[4-[3-[2-(−)-hydroxy-3-[4-(2-(cyclopropylmethoxy)ethyl)phenoxy]propylamino]propionamido]phenyl-5-methyl-4,5-dihydro-3(2H)-pyridazinone.

8. A compound according to claim 1 which is (−)-6-[4-[3-[2-(−)-hydroxy-3-[4-(2-(cyclopropylmethoxy)ethyl)phenoxy]propylamino]propionamido]phenyl]-5-methyl-4,5-dihydro-3-(2H)-pyridazinone substantially free of the corresponding (−) (+), (+) (−) and (+) (+)-isomers.

9. A compound according to claim 1 which is (−)-6-[4-[3-[2-(−)-hydroxy-3-[4-(2-(cyclopropylmethoxy)ethyl)phenoxy]propylamino]propionamido]phenyl]-5-methyl-4,5-dihydro-3(2H)-pyridazinone methanesulphonate substantially free of the corresponding (−) (+), (+) (−) and (+) (+)-isomers.

10. A pharmaceutical composition which comprises a compound according to claim 1 and a pharmaceutically acceptable carrier.

11. A pharmaceutical composition according to claim 10 which comprises 6-[4-[3-[2-hydroxy-3-[4-(2-(cyclopropylmethoxy)ethyl)phenoxy]propylamino]propionamido]phenyl]-5-methyl-4,5-dihydro-3(2H)-pyridazinone and a pharmaceutically acceptable carrier.

12. A pharmaceutical composition according to claim 10 which comprises 6-[4-[3-[2-hydroxy-3-[4-(2-cyclopropylmethoxy)ethyl)phenoxy]propylamino]propionamido]phenyl-5-methyl-4,5-dihydro-3(2H)-pyridazinone methanesulphonate and a pharmaceutically acceptable carrier.

13. A pharmaceutical composition according to claim 10 which comprises (−)-6-[4-[3-[2-(−)-hydroxy-3-[4-(2-(cyclopropylmethoxy)ethyl)phenoxy]propylamino]-propionamido]phenyl]-5-methyl-4,5-dihydro-3(2H)-pyridazinone and a pharmaceutically acceptable carrier.

14. A pharmaceutical composition according to claim 10 which comprises (−)-6-[4-[3-[2-(−)-hydroxy-3-[4-(2-(cyclopropylmethoxy)ethyl)phenoxy]propylamino]-propionamido]phenyl]-5-methyl-4,5-dihydro-3(2H)-pyridazinone substantially free of the corresponding (−) (+), (+) (−) and (+) (+)-isomers and a pharmaceutically acceptable carrier.

15. A pharmaceutical composition according to claim 10 which comprises (−)-6-[4-[3-[2-(−)-hydroxy-3-[4-(2-(cyclopropylmethoxy)ethyl)phenoxyl]propylamino]-propionamido]phenyl]-5-methyl-4,5-dihydro-3(2H)-pyridazinone methanesulphonate substantially free of the corresponding (−) (+), (+) (−) and (+) (+)-isomers and a pharmaceutically acceptable carrier.

16. A method of producing vasodilator and β-adrenoceptor antagonist activity which comprises administering to an animal an effective amount to produce said activity of a pharmaceutical composition according to claim 10.

17. A method of producing vasodilator and β-adrenoceptor antagonist activity which comprises administering to an animal an effective amount to produce said activity of a pharmaceutical composition according to claim 11.

18. A method of producing vasodilator and β-adrenoceptor antagonist activity which comprises administering to an animal an effective amount to produce said activity of a pharmaceutical composition according to claim 12.

19. A method of producing vasodilator and β-adrenoceptor antagonist activity which comprises administering to an animal an effective amount to produce said activity of a pharmaceutical composition according to claim 13.

20. A method of producing vasodilator and β-adrenoceptor antagonist activity which comprises administering to an animal an effective amount to produce said activity of a pharmaceutical composition according to claim 14.

21. A method of producing vasodilator and β-adrenoceptor antagonist activity which comprises administering to an animal an effective amount to produce said activity of a pharmaceutical composition according to claim 15.

22. A compound of formula (IA):

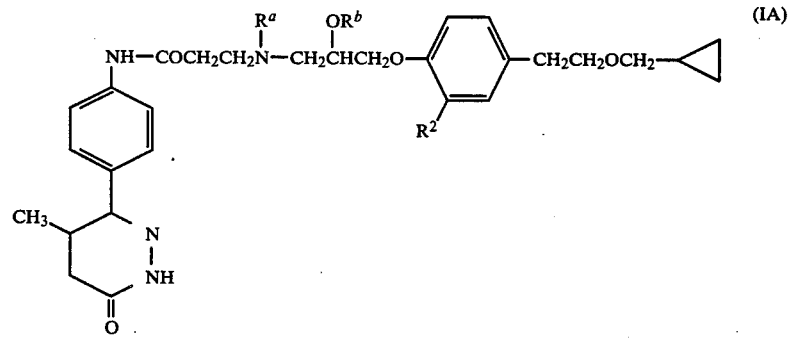

wherein $R^2$ is hydrogen, $C_{1-4}$alkyl or $C_{2-4}$alkylene, and $R^a$ and $R^b$ are independently hydrogen or amino or hydroxy protecting groups cleavable by hydrogenation or hydrolysis using conditions that do not substantially affect the remainder of the molecule, with the proviso that when $R^2$ is hydrogen or $C_{1-4}$alkyl, $R^a$ and $R^b$ are not both hydrogen.

23. A compound according to claim 22 wherein $R^2$ and $R^b$ are both hydrogen and $R^a$ is benzyl.

* * * * *